United States Patent [19]

Quentin-Millet et al.

[11] Patent Number: 5,045,203

[45] Date of Patent: Sep. 3, 1991

[54] SEPARATION OF PROTEIN ANTIGENS OF BORDETELLA BACTERIA BY AFFINITY CHROMATOGRAPHY

[75] Inventors: Marie-Jose Quentin-Millet, Villeurbanne; François Arminjon, Lyons, both of France

[73] Assignee: Pasteur Merieux Serums & Vaccins, Lyons, France

[21] Appl. No.: 629,674

[22] Filed: Dec. 18, 1990

Related U.S. Application Data

[62] Division of Ser. No. 38,748, Apr. 15, 1987, Pat. No. 4,985,144.

[30] Foreign Application Priority Data

Apr. 16, 1986 [FR] France .............................. 86 05457

[51] Int. Cl.$^5$ ............................................ B01D 15/08
[52] U.S. Cl. ................................... 210/635; 210/656; 210/198.2; 210/502.1; 502/403; 530/413; 530/417; 530/825
[58] Field of Search ................ 502/403; 210/635, 656, 210/198.2, 502.1; 530/413, 417, 825

[56] References Cited

U.S. PATENT DOCUMENTS

| | | | |
|---|---|---|---|
| 4,010,251 | 3/1977 | Green | 530/387 |
| 4,125,492 | 11/1978 | Cuatrecasas | 530/413 |
| 4,225,487 | 9/1980 | Cuatrecasas | 530/413 |
| 4,247,452 | 1/1981 | Irons | 530/413 |
| 4,308,254 | 12/1981 | Tayot | 424/87 |
| 4,416,872 | 11/1983 | Alving | 530/395 |
| 4,466,951 | 8/1984 | Pittman | 530/810 |
| 4,612,121 | 9/1986 | Hermansson | 210/635 |

FOREIGN PATENT DOCUMENTS

| | | | |
|---|---|---|---|
| 0003916 | 9/1979 | European Pat. Off. | 210/635 |
| 0140386 | 5/1985 | European Pat. Off. | 210/198.2 |
| 547104 | 3/1985 | U.S.S.R. | 502/403 |
| 2006642B | 4/1979 | United Kingdom | 210/198.2 |
| 2015531A | 9/1979 | United Kingdom | 210/198.2 |

OTHER PUBLICATIONS

Murray, The Indentification of Oral Microbial Lectins by Cell Affinity Chromatography, FEMS Microbiol. Lett., (40(1), pp. 123–127.
Lee, "Preparation of a High-Affinity Photolabeling Reagent for the Gal/GalNAc Lectin of Mammalian Liver," Biochemistry, 1986, vol. 25, No. 22, 1986.
Robinson, "Porous Glass As A Solid Support for Immobilization or Affinity of Enzymes", Biochim. Biophys. Acta, 242(1971), pp. 659–661.
"Porous glass as a solid support for immobilisation or affinity chromatography of enzymes", *Biochimica et Biophysica Acta Robinson*, Dunnill & Lilly, Aug. 1971, pp. 659–661.
Proceedings of the Pertussis Toxin Conference, Bethesda, Md., Sep. 1984, Edited by R. D. Sekua et al., Acad. Press Inc., pp. 45–64 (1985).
"Structure of the Complex Oligosaccharides of Fetuin", *Journal of Biological Chemistry, vol. 254, No. 3 (1979), 789–795.*
"Structure of the O-Glycosidically Linked Carbohydrate Units of Fetuin", *The Journal of Biological Chemistry*, vol. 249, No. 18, (1974) pp. 5704, 5717.
Proceedings of VI International Symposium on Glycocconjugata (1981), pp. 275–276 "The Carbohydrate Structure of Human Haptoglobin".
Biological Abstracts, vol. 58, No. 12, Dec. 15, 1974, p. 6941, No. 64553–Hudgin et al.
Chemical Abstracts, vol. 74, No. 19, May 10, 1971, p. 187, No. 96321g–Morell et al.
J. Biol. Chem . 231, No. 23, 1976, pp. 7581–7687, "Isolation and Proterties of Beta–Galctoside Binding Lectins of Calf Heat and Lung", by Waard et al.
Biochemical and Biophysical Research Communication, vol. 122, No. 3, 1984, pp. 938–944, "Human Placenta Beta–Glactoside Binding Lectin. Purification and Some Properties", by Hirabayashi et al.

*Primary Examiner*—Ernest G. Therkorn
*Attorney, Agent, or Firm*—Cushman, Darby & Cushman

[57] ABSTRACT

A chromatography material comprises a solid support on which is fixed, as a ligan, desialyled gycolprotein selected from desialyled fetuin and desialyled haptoglobin. This material is used to purify protein antigens of bacteria of the Bordetella genus.

5 Claims, No Drawings

SEPARATION OF PROTEIN ANTIGENS OF BORDETELLA BACTERIA BY AFFINITY CHROMATOGRAPHY

This is a division of application Ser. No. 07/038,748, filed Apr. 15, 1987, now U.S. Pat. No. 4,985,144.

The present invention relates to a new affinity chromatography material and to its use principally in the separation and purification of protein antigens of bacteria belonging to the Bordetella genus.

It is known that the culture of bacteria of the Bordetella genus, for example, *Bordetella pertussis, Bordetella parapertussis* and *Bordetella bronchiseptica*, yields the F-HA protein (Filamentous hemagglutinin). Moreover, the culture of *B-pertussis* toxin, also yields a protein exotoxin: pertussis toxin, also called LPF or LPF-HA (Leukocytosis Promoting Factor-Hemagglutinin). These proteins can be employed principally in the preparation of acellular anti-whooping cough vaccines.

The separation and purification of protein antigens of bacteria of the Bordetella genus so as to obtain purified antigens with good yields pose technical problems which are difficult to resolve.

Generally, affinity chromatography techniques are employed in a purification operation.

In U.K. patent application No. 2,015,531 there is envisaged an affinity chromatography process using an insoluble polymeric support on which is fixed a sialoprotein or another substance rich in sialic acid. The sialoprotein selectively fixes pertussis toxin which can then be eluted.

In European patent application No. 0140386 there is described a chromatography process using as the ligand selective for pertussis toxin a heat denatured ceruloplasmin.

It has now been discovered, in a surprising manner, that pertussis toxin has a greater affinity for desialyled glycoproteins immobilized on a support than for sialoproteins, as will be shown hereafter. This result is all the more surprising since in the case where pertussis toxin is immobilized on the support it has been observed that fetuin inhibits the fixation of fetuin labelled with iodine 125 more than does asialofetuin (93% inhibition only with respect to fetuin); see R. D. Sekura et al., "Pertussis Toxin Structural Elements Involved in the Interaction With Cells", Proceeding of the Pertussis Toxin Conference, Bethesda, Md., Sept 20-21, 1984 edited by R. D. Sekura, J. Moss and M. Vaughan 1985, Academic Press Inc., pages 45-64.

The present invention relates to the use, as an affinity chromatography ligand for pertussis toxin, desialyled glycoprotein. The desialyled glycoprotein can be selected, in particular, from desialyled fetuin and desialyled haptoglobin.

It is known that fetuin and haptoglobin contain sialyled oligo-osidic groups; see for example J. U. Baenziger et al, the Journal of Biological Chemistry, Vol. 254, No. 3, p. 789-795 (1975) and B. Nilsson et al, Proceedings of VI International Symposium on glycoconjugates (1981), pages 275-276.

The acid hydrolysis of fetuin or haptoglobin, in accordance with known methods, converts the sialyled osidic structures into corresponding desialyled osidic structures, and there are thus obtained asialofetuin or asialohaptoglobin.

Fetuin and haptoglobin are commercial products sold principally by Sigma.

The present invention also relates to a new affinity chromatography material comprising a solid support on which is fixed a ligand having an affinity for pertussis toxin, said ligand being a desialyled protein selected from the group consisting of desialyled fetuin and desialyled haptoglobin.

These proteins, before or optionally after being coupled to the solid support are subjected to a desialylation treatment. This desialylation treatment is effected by mild hydrolysis in accordance with known methods; see for example R. G. Spiro et al, J. Biol. Chem. 1974, 249, 5704-5717.

The solid support to which the desialyled protein is coupled can be any conventional solid support generally employed in affinity chromatography.

The support is, for example, a polymeric support comprising a polyosidic derivative, a polyacrylamide, a polymer or copolymer containing N-acryloyl-2-amino-2-hydroxymethyl-1,3-propanediol units such as supports sold by I.B.F. (Institut Biologique Francais) under the trade names "TRISACRYL".

Representative useful polyosidic derivatives include, in particular, cellulose, dextran, agarose, sepharose, starch as well as polyosidic derivatives modified by etherification with aminated alcohol derivatives. These modified polyosidic derivatives have the formula 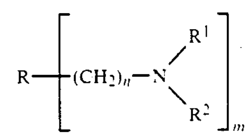 wherein R represents the residue of the polyoside, m is a whole number ranging from 1 to 10 and preferably from 2 to 5, $R^1$ and $R^2$ represent lower alkyl or hydroxy lower alkyl and n represents the number of etherifying groups fixed on the polyosidic molecule.

Representative modified polyosidic derivatives include, for example, diethylaminoethyl cellulose (DEAE cellulose), DEAE dextran, DEAE starch and the like.

The polymers used as supports can themselves be fixed on a porous mineral support comprising, for example, a metallic oxide such as silica, alumina, magnesia, etc, or natural or synthetic derivatives of these oxide such as glasses, silicates, borosilicates, kaolin etc.

The said polymers can be fixed on the porous mineral support by impregnation, the polymer coating then being, if necessary, stabilized by crosslinking in accordance with known methods. The crosslinking agent is, for example, a dicarbonyl compound, a halohydrin, a diepoxide, etc. The polymer supports can also be fixed on mineral supports by means of an intermediate bifunctional coupling agent.

The desialyled proteins can also be fixed on the polymeric support by means of an appropriate bifunctional coupling agent, in accordance with known methods. The coupling agents are, for example, bifunctional derivatives such as cyanogen bromide, dialdehydes, diepoxides, etc.

The desialyled proteins can also be directly fixed on the porous mineral support.

For example, in the case of a silica support, an aminoalkylsilane derivative of silica, is prepared and the desialyled protein is fixed on the aminoalkylsilane using a bifunctional agent such as glutaraldehyde; see for example P. J. Robinson et al, Biochem. Biophys. Acta, 242, 659-661 (1971).

The desialyled proteins can also be fixed on porous mineral supports in accordance with the method described in French patent application 77.28163 (publication No. 2.403.098). This process comprises coating a porous mineral support with a polyosidic polymer capable of undergoing a cleavage reaction oxidizing the glycol groups using oxidizing agents such as periodates. A polycarbonyl coating is obtained and the ligand, for example, the desialyled glycoprotein, can then be fixed on the carbonyl groups formed. If desired, the imine group formed can be reduced to the amine.

The present invention also relates to a process for purifying protein antigens of bacteria belonging to the Bordetella genus. This process comprises, essentially, contacting a solution containing the said protein antigens with an affinity chromatography support such as defined above, then collecting or eluting the sought after antigens.

In this fashion the pertussis toxin which is fixed on the affinity chromatography support is separated from the solution whereas the F-HA remains in solution. The pertussis toxin is then eluted with an appropriate elution agent.

The process of the present invention can also be employed to purify a fraction enriched in F-HA in a manner so as to eliminate any pertussis toxin that the fraction may contain, the latter, i.e., the pertussis toxin being retained by the affinity chromatography support. By separating the solution obtained after contact with the chromatography material, a purified solution of F-HA is obtained.

The starting solution to be purified can be, for example, the culture supernatant of bacteria of the Bordetella genus or a partially purified solution of pertussis toxin or F-HA.

To purify pertussis toxin on the affinity chromatography support of the present invention, a starting solution is employed whose pH has been adjusted to a value of 6-8 and preferably to a value of 7.

The amount of the affinity chromatography support employed in a function of the volume of initial supernatant and/or the pertussis toxin concentration in the culture medium or in the fraction employed as the starting product. Contact is carried out in a bath or in a column at a temperature of 2°-30° C.

To elute pertussis toxin fixed on the affinity chromatography support of the present invention, there can be employed, for example, a buffer solution containing, at a sufficient concentration, salts and/or known chaotropic agents, such as, magnesium chloride, or even a carbonate buffer having a molarity greater than 25 $\mu$M and whose pH is of the order of 8.3 to 11.6.

The following non-limiting examples are given to illustrate the invention.

EXAMPLE 1

Purification of pertussis toxin by affinity chromatography on Sepharose 4B - asialofetuin (a) Adsorption of pertussis toxin on an affinity chromatography gel.

A fraction enriched in pertussis toxin, obtained after centrifugation and concentration of a bacteria suspension of *Bordetella pertussis* phase I, cultivated in a 30 liter fermentor, is passed through a 4 cm diameter column containing 120 ml of, as the chromatography support, Sepharose 4B coupled to asialofetuin, at a flow rate of 6 ml/cm²/hour.

The Sepharose 4-B was coupled to the asialofetuin in the following manner.

30 g of Sepharose 4-B, activated by CNBr, (Pharmacia) are swollen in 6 liters of 1 mM HCl for about 15 minutes. The gel is then washed three times with 6 liters of 1 mM HCl. 400 ml of a solution containing 1 mg/1 ml of asialofetuin, 0.1M NaHC0$_3$ and 0.5M NaCl are added to the gel.

The mixture is left overnight to react at +4° C. with mild stirring. 125 ml of a 5M solution of ethanolamine, pH 8, are added to the reaction mixture. After 4 hours of incubation at ambient temperature, the gel is washed successively with 500 ml of 0.1M sodium acetate buffer, pH 4.0, containing 1M NaCl, then with 500 ml of 50 mM Tris-HCl buffer, pH 7.5, containing 1M NaCl. This washing cycle is repeated three times.

The gel is then washed three times with 500 ml of 50 mM Tris-HCl buffer, pH 7.5, in the presence of a preservative such as merthiolate at a concentration of 1/10,000 (w/v).

The Sepharose 4B gel coupled to asialofetuin is maintained at +4° C. in a buffer such as 50 mM Tris-HCl buffer, pH 7.5 in the presence of a preservative such as merthiolate.

The asialofetuin, employed as the ligand in the affinity chromatography, was obtained in the following manner.

An aqueous solution of fetuin (type III fetuin, Sigma) is hydrolyzed by 0.05N H$_2$SO$_4$ for 1 hour at 80° C. After hydrolysis, the solution is dialyzed against several distilled water baths for 24 hours at +4° C. in order to remove free sialic acids. The asialofetuin solution can be concentrated by ultrafiltration with a system equipped with membranes whose cut-off threshold is equal to 10,000.

The removal of the sialic acids is controlled by a specific colorimetric dosage of the sialic acids on the protein, before and after hydrolysis.

(b) Elution of the pertussis toxin.

The gel is washed with two column volumes of 50 mM Tris-HCl buffer, pH 7.5, that is, until a complete disappearance of UV absorption at 278 nm, then with one column volume of 50 mM Tris-HCl buffer, pH 7.5, containing 1M NaCl. The pertussis toxin is eluted with 400 ml of 100 mM carbonate buffer, pH 9.6.

The optical density and the hemagglutinating activity of the fractions collected at the exit of the column are measured.

The fractions containing the active principle, i.e. cells having a strong hemagglutinating activity, non-inhibited by cholesterol, are combined.

The pertussis toxin is then precipitated by ammonium sulfate at a final concentration corresponding to 70% of saturation.

The resulting purified pertussis toxin induces a strong lymphocytosis and sensitizes CFW mice to histamine at a dosage of 0.04 $\mu$g/mouse. The capacity of the toxin to induce the formation of clusters on HOC cells (hamster ovary cells) is characterized by a specific activity of the order of 65,000 to 260,000 CPU/mg.

The results of physico-chemical controls and biologic activities (colorimetric dosages of possible contaminants, DNA, RNA, sugar; dosage of the amount of endotoxin, electrophoresis in SDS medium or in acid medium, etc) are indicative of a final homogeneous preparation containing a highly purified active principle.

The analysis of the amount of pertussis toxin in the supernatant of the initial culture and in the final precipitate indicates a purification yield greater than 90%.

EXAMPLE 2

Purification of pertussis toxin by affinity chromatography on DEAE dextran - asialofetuin Spherosil (a) Adsorption of the toxin on the affinity chromatography gel.

The pH of the fraction obtained after centrifugation and concentration of a suspension of *Bordetella pertussis* phase I is adjusted to 7.0 by the addition of a 5N HCl solution. The fraction is passed through a 2 cm diameter column containing 60 ml of, as the chromatography support, Spherosil DEAE dextran coupled to asialofetuin, at a flow rate of 60 ml/cm$^2$/hr.

The Spherosil DEAE dextran (support made of small XOC 005 silicon balls coated with a minimum of cross-linked DEAE dextran) was coupled to the asialofetuin in the following manner.

Spherosil DEAE dextran is submitted to controlled oxidation in order to create aldehyde functions capable of reacting with amine groups of the ligand. The asialofetuin in solution, at a concentration of 4 mg/ml, in a 10 mM phosphate buffer, pH 8.0, is contacted with the gel for 15 hours at ambient temperature. The gel is then washed with the following solutions:

10 mM phosphate buffer, pH-8.0,
glycocol 20 g/l, 0.17M NaCl,
0.05 sodium citrate, pH 2.8, 0.1N HCl.

(b) Elution of pertussis toxin

The gel is washed with 120 ml of 50 mM Tris-HCl buffer, pH-7.5, then with 70 ml of 50 mM Tris-HCl buffer containing 1M NaCl. The pertussis toxin is eluted with 50 mM Tris-HCl buffer, pH-7.5, containing 4M $MgCl_2$. The optical density at 278 nm and the hemagglutinating activity of the fractions collected at the exit of the column are measured. The fractions containing the active principle, i.e., the cells having a high hemagglutinating activity non inhibited by cholesterol are combined.

Salt is removed from the resulting mixture by gel filtration in a Sephadex G-25 column (7.5×45 cm, Pharmacia) equilibrated with 50 mM Tris-HCl buffer, pH-7.5. The elution is carried out with this same buffer.

The optical density at 278 nm and the hemagglutinating activity of the fractions collected at the exit of the columns are measured. The fractions containing pertussis toxin, i.e. cells having a high hemagglutinating activity are combined.

The active principle is precipitated by ammonium sulfate by the slow addition, with stirring, of 47 g of $(NH_4)_2SO_4$ per 100 ml of solution. Analysis of the biologic and physicochemical properties show that the resulting product is a highly purified active principle.

EXAMPLE 3

Removal of possible traces of pertussis toxin in a F-HA enriched fraction

Known processes for the purification of F-HA, as described for instance in the publication of Y. Sato, J. L. Cowell, H. Sato, D. G. Burstyn and C. R. Manclark, entitled "Separation and purification of the hemagglutinins from *Bordetella pertussis*", Infect and Immun., 1983, 41, 1, 313–320, include the desorption of the starting F-HA using a chromatography support such as hydroxyapatite and 100 mM phosphate buffer, pH 7.0, containing 0.5M NaCl.

The optical density at 278 nm and the hemagglutinating activity of the fractions recovered at the exit of the hydroxyapatite column are measured. The F-HA containing fractions, i.e. cells having a high hemagglutinating activity and inhibited by cholesterol are combined.

In the present invention, in order to remove the last traces of pertussis toxin that may possibly be present, the mixture of fractions containing F-HA is passed through a Sepharose 4B asialofetuin column. The F-HA is eluted directly whereas any traces of the pertussis toxin are retained on the column.

The F-HA is then precipitated with ammonium sulfate by slowly adding, with stirring, 47 g of $(NH_4)_2SO_4$ per 100 ml of solution.

The resulting purified F-HA induces neither lymphocytosis nor sensitization to histamine at a dosage of 100 μg/mouse. At a concentration of 100 μg/ml, F-HA does not cause modification of the appearance of the cellular mass constituted by hamster ovary cells (HOC), i.e. the formation of a cellular mass called "clusters" which is characteristic of the presence of pertussis toxin. Its specific hemagglutinating activity measured on goose erythrocyctes is in the order of 250,000 to 500,000 HA/mg protein units. This activity is completely inhibited by cholesterol.

EXAMPLE 4

Comparative study of the fixation capacity of pertussis toxin by the affinity chromatography supports based on fetuin and asialofetuin An affinity chromatography gel was prepared by the immobilization of asialofetuin on Sepharose 4B, activated with CNBr (Pharmacia), in accordance with the procedures set forth in Example 1.

In a similar manner an affinity chromatography gel was prepared using fetuin.

The fixation of fetuin and the fixation of asialofetuin have been effected under identical experimental conditions so as to obtain gels having comparable ligand densities. A comparative study of the capacity of the resulting gels was carried out. The results are set forth in the following table wherein an efficiency of 100% has arbitrarily been assigned to the gel based on asialofetuin.

| | Relative Capacity of the gel (%) |
|---|---|
| Fetuin-Sepharose-4B | 79 |
| Asialofetuin-Sepharose-4B | 100 |

The indicated values are the result of two measurements. Each experiment was carried out in parallel on the two types of supports by contacting them with the same volume of culture supernatant containing pertussis toxin. The amount of pertussis toxin eluted has been determined by a dosage of protein and by an immunoenzymatic method (ELISA).

What is claimed is:

1. A process for purifying protein antigens of bacteria of the Bordetella genus comprising contacting a solution containing said protein antigens with a chromatography material comprising a solid support on which is fixed a ligand having an affinity for pertussis toxin, said ligand being a desialyled protein selected from the group consisting of desialyled fetuin and desialyled haptoglobin and collecting or eluting the desired antigens.

2. The process of claim 1 wherein said ligand is fixed on a polymeric support.

3. The process of claim 2 wherein said polymeric support is fixed on a porous mineral support.

4. The process of claim 1 wherein subsequent to contacting said solution with said chromotagraphy material, pertussis toxin is eluted from said material.

5. The process of claim 1 wherein said solution to be contacted with said chromatography material is a fraction enriched in F-HA and that subsequent to contacting said fraction with said chromatography material a purified solution of F-HA free of pertussis toxin is collected.

* * * * *